United States Patent

Stouffer et al.

[11] 3,973,558
[45] Aug. 10, 1976

[54] SWEPT JET ORAL IRRIGATOR

[75] Inventors: Ronald D. Stouffer, Silver Spring; Peter Bauer, Germantown, both of Md.

[73] Assignee: Bowles Fluidics Corporation, Silver Spring, Md.

[22] Filed: Sept. 30, 1974

[21] Appl. No.: 510,701

[52] U.S. Cl. .............................. 128/66; 128/DIG. 10
[51] Int. Cl.² ......................................... A61H 9/00
[58] Field of Search ............... 128/62 A, 66, 38–40, 128/24.1, 24.2, DIG. 10

[56] References Cited
UNITED STATES PATENTS

| | | | |
|---|---|---|---|
| 1,995,424 | 3/1935 | Guinness | 128/66 |
| 3,452,745 | 7/1969 | Hutchinson et al. | 128/66 |
| 3,507,275 | 4/1970 | Walker | 128/66 X |
| 3,547,110 | 12/1970 | Balamuth | 128/66 |
| 3,593,707 | 7/1971 | Pifer | 128/62 A |
| 3,753,435 | 8/1973 | Blasnik | 128/66 |

*Primary Examiner*—Lawrence W. Trapp
*Attorney, Agent, or Firm*—Rose & Edell

[57] ABSTRACT

An improved oral irrigation technique is characterized by an oscillatory swept water jet issued to sweep back and forth at high frequencies across the user's gums and teeth. High frequency operation is achieved by oscillating the jet itself rather than the jet-issuing body. The high frequency sweeping jet effects faster cleaning action and more effective gum massage than prior art pulsed jet irrigators having lower effective operating frequencies.

14 Claims, 13 Drawing Figures

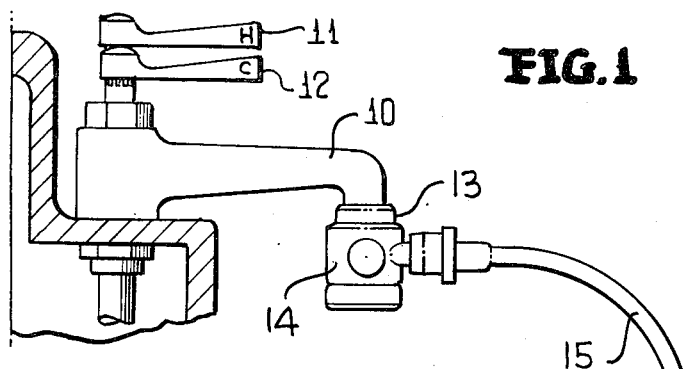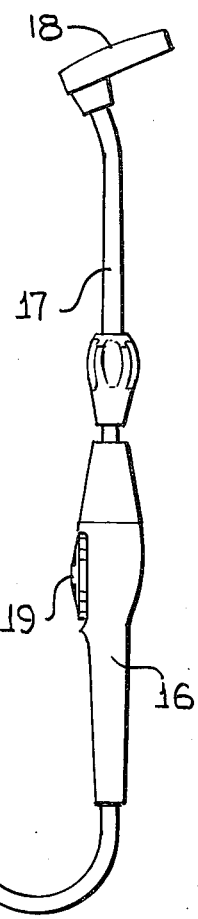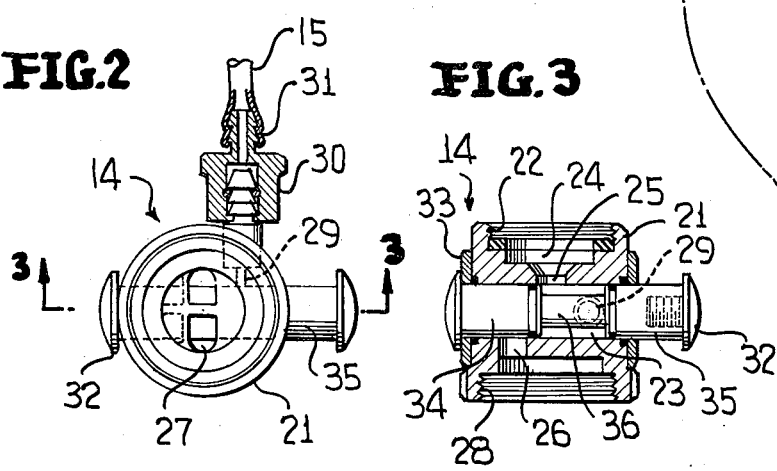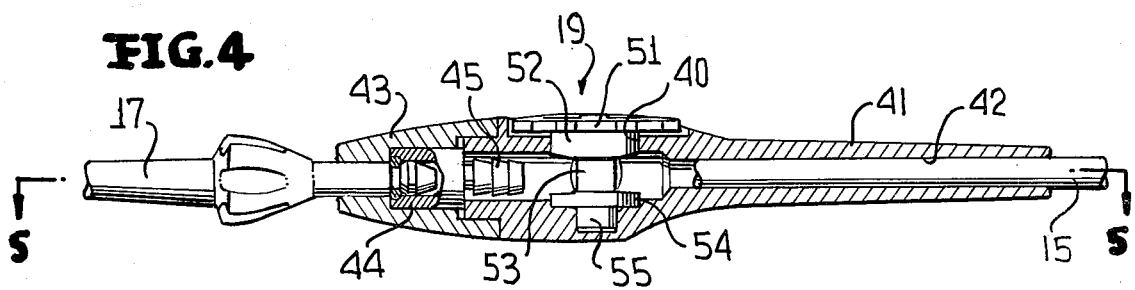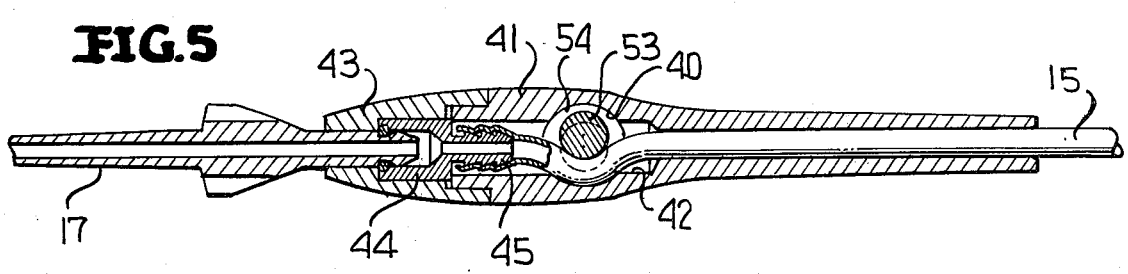

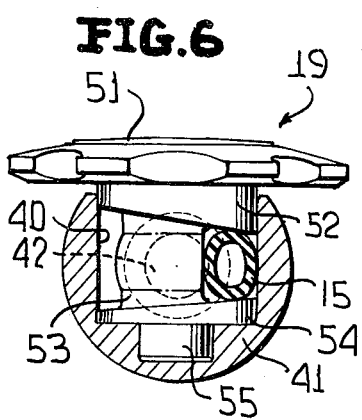
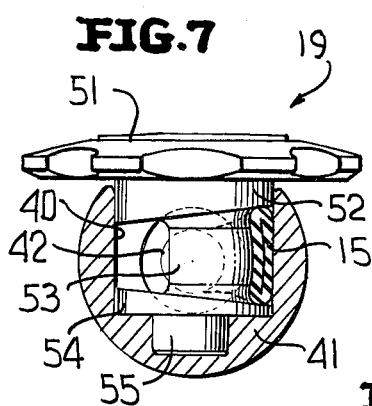
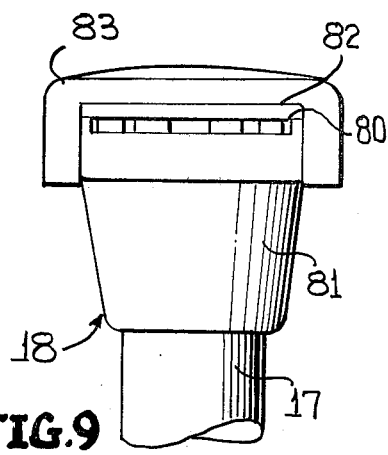
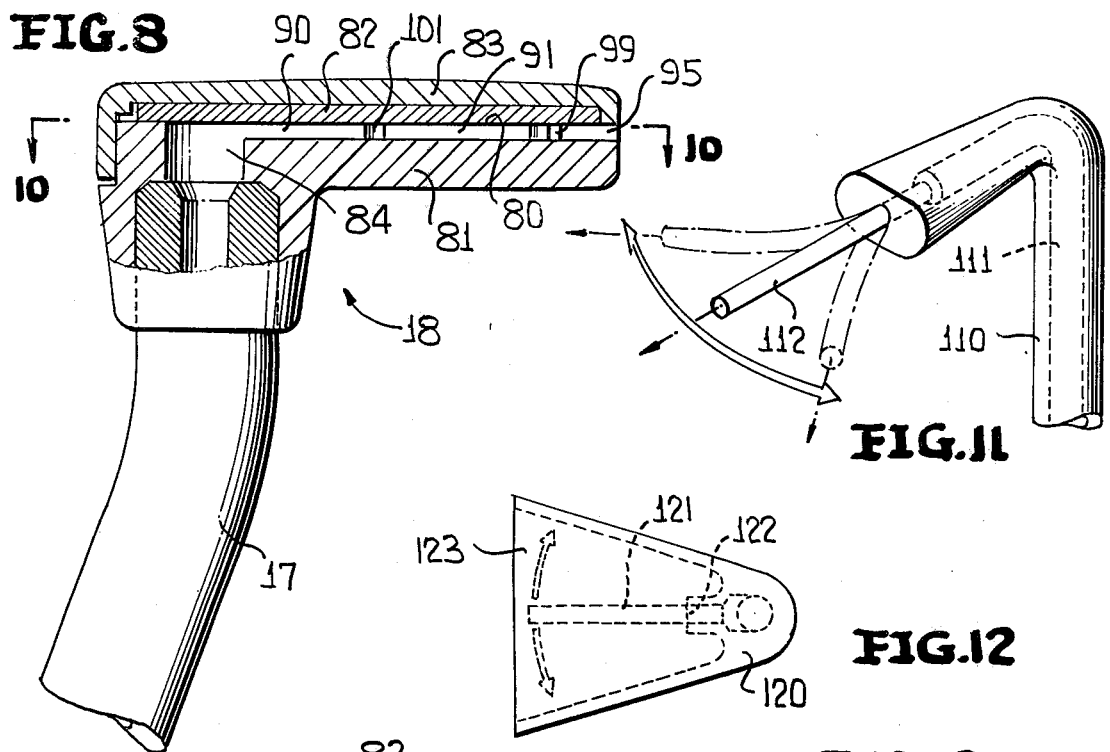
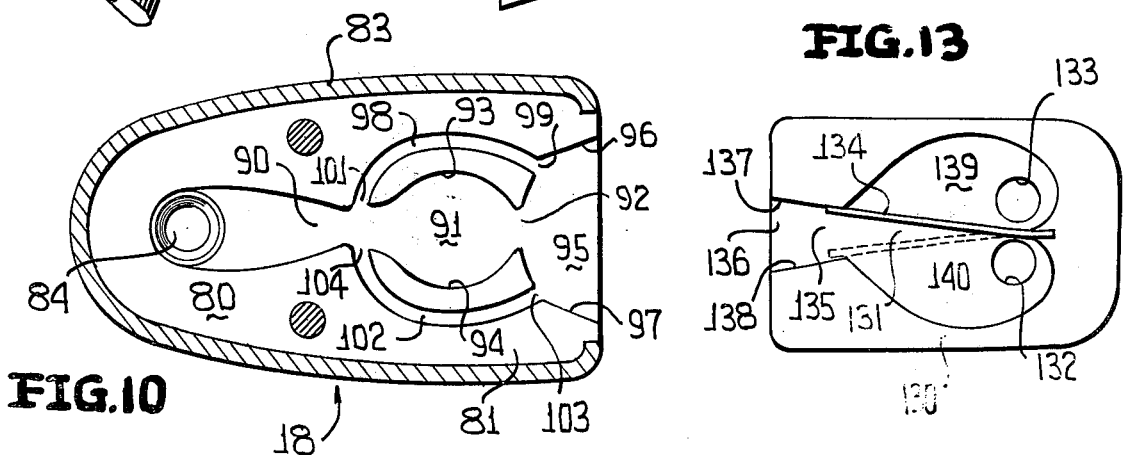

SWEPT JET ORAL IRRIGATOR

BACKGROUND OF THE INVENTION

The present invention relates to improvements in oral irrigation and, more particularly, to a novel method and apparatus for employing water under pressure to cleanse and massage the user's oral cavity.

Oral irrigators are well known in the prior art. One such apparatus, as described in U.S. Pat. No. 3,227,158 to Mattingly, issues a pulsed water jet through a nozzle under the driving action of an electrically-operated pump. The pulse act to massage the user's gums and loosen food particles lodged between the teeth and between the teeth and gums. In order to provide an effective gum massage, the repetition rate of the pulses is selected to permit the user's gums to rebound from their depressed state between successive pulses. Typically this repetition rate is on the order of 1000 to 1600 pulses per minute.

Subsequent developments recognized certain disadvantages in the Mattingly approach and set out to provide improvements. For example, U.S. Pat. No. 3,542,017 to Adams points out the shock hazard involved in using an electrically-operated pump and the cumbersome nature of the overall apparatus. To this end, Adams employs a fluidic oscillator to supply the pulsating water jet, the oscillator requiring no moving parts, whereby the requirement for an electrically-operated pump is eliminated. Adams makes no mention of the pulse repetition rate in his patent; however, in view of Mattingly's analysis, for effective massage the pulsed jet repetition rate must be on the order of 1000 to 1600 pulses per minute in order to permit the gum the rebound between pulses. There is a major practical disadvantage associated with the Adams irrigator. Specifically, the oscillating power stream in the fluidic oscillator must be oscillated between one outlet passage which feeds the outlet tube and a second outlet passage which serves as a vent. The venting wastes half of the applied water, a factor which is an anathema to present day stress on water conservation.

Still another prior art approach is illustrated in U.S. Pat. No. Re. 26,589 to Murov et al. The oral irrigator disclosed in that patent also avoids the use of electricity by using the pressure of the water to reciprocate the irrigator outlet tube. As a consequence, liquid is translated back and forth across the gums as the outlet tube reciprocates. The reciprocating drive mechanism in this device renders the device somewhat bulky and subject to failure because of the wear and tear between moving parts. Moreover, there is a practical limit to the frequency at which the outlet tube can be reciprocated.

It is therefore an object of the present invention to provide an oral irrigator which is operated solely by the applied tap water and has minimal pressure loss downstream of the oscillator, and utilizes all of the applied water in the irrigating flow.

It is another object of the present invention to provide an oral irrigator which can operate at substantially higher frequencies than prior art devices without sacrificing any effectiveness in its gum massaging action.

It is also an object of the present invention to provide a method of oral irrigation wherein tap water serves as the sole power source, pressure loss downstream of the oscillatory member is minimized and water waste is eliminated.

It is still another object of the present invention to provide a method of oral irrigation wherein operating frequencies far in excess of those employed in the prior art can be used without sacrificing effective gum massaging.

SUMMARY OF THE INVENTION

We have found that an oscillating water jet can be swept back and forth over the user's teeth and gums at relatively high frequency with superior cleaning results and massaging effects as compared to prior art devices. The sweeping jet breaks up into multiple droplets which successively impinge upon adjacent gum locations. The recess created in the gum by one impacting droplet is forced back to its initial contour by the next droplet as it recesses the adjacent location. The overall effect may be viewed as an undulating wave along the gum surface wherein each droplet recesses the gum at its point of impact but forces the gum to rebound in the immediately surrounding areas. Since rebound time for the gum is not limited by the gum's own elasticity, high sweep frequencies may be employed. In fact, sweep frequencies on the order of 20,000 cycles per minute have been tested and found to provide effective massaging action along with a more sensually pleasurable effect on the user than is obtained with prior art devices. In addition, the high frequency swept water jet acts to sweep food particles out of lodged positions whereby the prior art pulsed jet sometimes forces the particles deeper between the teeth or between the gums and teeth, a characteristic which many dentists find objectionable. Thus, where the swept jet continuously moves of and by itself, the pulsed jet must be moved by the user to avoid the aforementioned problem and to have any real effect.

In order to achieve the high frequency sweeping action, the jet itself is oscillated rather than the irrigator stem. Further, oscillation is effected at the head of the irrigator stem whereby the sweeping jet is issued directly into the user's oral cavity from the oscillating means without experiencing pressure drops in the irrigator stem. The oscillating means is powered by the applied water pressure alone and may be fluidic oscillator, a vibratable reed, a self-oscillating flexible tube, or the like.

The irrigator may be modified to include bristle members on the head which take advantage of the vibrations set up in the stem by the sweeping means to effect a high frequency brushing action. Alternatively, an oscillator may be employed at some brushing frequency while the sweeping means operates at some higher irrigating frequency.

The irrigator is further characterized by a control valve in the handle and a diverter valve in the tube attaching to the water spigot. These valves, in combination with the facuet valves on the spigot itself, permit the following functions to be achieved: (1) setting the desired water temperature, independently of pressure, witih the faucet valves; (2) coarsely setting the desired water pressure, independently of temperature, with the diverter valve; and (3) finely adjusting the pressure, and also permitting testing of the temperature without the necessity for passing water through the irrigator.

BRIEF DESCRIPTION OF THE DRAWINGS

The above and still further objects, features and advantages of the present invention will become apparent upon considerable of the following detailed description of specific embodiments thereof, especially when taken in conjunction with the accompanying drawings, wherein:

FIG. 1 is a view in elevation showing an oral irrigator according to the present invention in its operative condition attached to a faucet feature;

FIGS. 2 and 3 are bottom and side sectional views, respectively, in plan of a diverter valve employed with the irrigator of the present invention;

FIGS. 4 and 5 are top and side plan views, respectively, of the handle of the irrigator of the present invention;

FIG. 6 is a side view in plan of a control valve employed in the handle of FIGS. 4 and 5, the valve being shown in the on position;

FIG. 7 is a side view in plan of the control valve of FIG. 6 shown in the off position;

FIGS. 8, 9 and 10 are side, end and top plan views, respectively of the head portion of a preferred embodiment of the oral irrigator of the present invention;

FIG. 11 is a diagrammatic illustration of an alternative jet sweeping arrangement for the head of the oral irrigator;

FIG. 12 is a plan view of an oral irrigator head employing the jet sweeping arrangement of FIG. 11; and FIG, 13 is a plan view of an oral irrigator head employing still another alternative jet sweeping arrangement.

DESCRIPTION OF PREFERRED EMBODIMENTS

Referring in detail to FIG. 1 of the accompanying drawings, an oral irrigator apparatus is connected to the spigot 10 of a sink faucet fixture having a hot water control valve 11 and a cold water control valve 12. The irrigator apparatus is attached to the spigot by a threaded adaptor 13, if necessary, to which a diverter valve 14 is secured. A flexible conduit or hose 15 directs water flow from diverter valve 14 to the inlet end of a handle member 16. A stem 17 is removably secured at one end to the outlet end of handle 16. The other end of stem 17 terminates in a sweep head 18. Water delivered by conduit 15 to the handle 16 is passed hrough the handle under the control of a control valve 19 to sweep head 18 where the water flow is caused to oscillate in a manner to be described subsequently. The oscillating stream is issued from head 18 in a sweeping pattern which diverges in a downstream direction. Stem 17, with head 18 attached, may be interchanged with other stems so that each member of a family may have a separate stem and head for use with a common handle and hose.

In use, the head 18 is inserted into the oral cavity of the user so that the sweeping water jet may impinge upon the teeth and gums. In so doing the jet effectively sweeps away food and dirt particles lodged between teeth and between the teeth and gums. In addition, the sweeping jet provides a therapeutic and sensually pleasing massaging action on the gums. One reason for the sensually pleasing effect is the sensation of sweeping across the gum surface as compared to a repetitive pounding of the same location as occurs in oral irrigators of the pulsed jet type. Another reason for the sensually pleasing effect is the higher frequency of operation permitted by a sweeping jet massage than is possible for a pulsed jet massage. Specifically, a pulsed jet oral irrigator is limited in its useful repetition rate by the elasticity of gum tissue. The pulses must be sufficiently spaced in time to permit the tissue to rebound from a depression caused by each pulse. If the tissue is not permitted to rebound, successive pulses produce minimal blood circulation and, in some instances, cause significant pain. As a practical matter, therefore, pulsed jet oral irrigators are designed to operate at repetition rates below 2000 pulses per minute. With the sweeping jet, however, the jet breaks up into discrete droplets which successively impinge upon adjacent gum locations. As each droplet depresses the gum at its point of impact, it also forces the adjacent area, including the previously recessed point, back to its unrecessed position. This forcing of the gum back to its normal position increases the rebound time by at least an order of magnitude over the normal or unaided rebound time. Consequently, the sweeping jet can be swept at considerably higher frequencies than the repetition rates usable in pulsed jet irrigators. By way of example, whereas pulsed jet oral irrigators are limited to repetition rates below 2000 pulses per minute, our swept jet oral irrigator is operable at 20,000 cycles per minute. At this higher frequency, the swept jet oscillator rapidly undulates the gum surface to produce a more effective blood circulation and massaging action; it also sweeps away food particles more rapidly than the slower frequency pulsed jet device.

Referring to FIGS. 2 and 3 of the accompanying drawings, diverter valve 14 includes a hollow generally cylindrical body member 21 which is internally threaded at its open upper end 22 to engage either a suitable adapter or spigot. The interior opening 24 of body member 21 converges in discrete steps in a longitudinal direction to form an internal orifice 25 positioned about the longitudinal axis of body 21. A bore 23 is defined diametrically through body 21, with orifice 25 terminating at the bore sidewalls. A first egress opening 26 is defined through the opposite sidewall of bore 23 but displaced from the longitudinal axis of body 21. Egress opening 26 and orifice 25 are arranged such that no part of either one is in longitudinal alignment with any part of the other. Egress opening 26 communicates with openings 27 in the bottom end 28 of body 21.

A second egress opening 29 is defined through the sidewall of bore 23 at a location 90° displaced from orifice 25 and egress opening 26. In addition, egress opening 29 is displaced to the opposite side of the longitudinal axis of body 21 from egress opening 26. One end of a connector 30 extends transversely through body member 21 into sealed flow communication with egress opening 29, the other end of connector 30 terminates in a fitting 31 to which hose 15 (see FIG. 1) may be secured.

A generally cylindrical shuttle member 32, which is longer than the diameter of body 21, is captured within bore 23 by a retainer ring 33. Shuttle member 32 has two end sections 34, 35 of diameter substantially equal to that of bore 23. A middle section 36 of shuttle 32 has a substantially smaller diameter. The length of section 36 is such to permit flow communication between orifice 25 and egress opening 26 in one extreme position of the shuttle and to permit flow communication between orifice 25 and egress opening 29 in the other extreme position of the shuttle. Flow from orifice 25 to either of egress openings 26 and 29 may therefore be blocked depending upon the shuttle position.

When flow is to egress through opening 26 only, water from the faucet falls into the sink and its temperature may be easily determined by the user. Thereafter, the user may shift the shuttle until the roughly desired flow rate is achieved through egress opening 29 and the irrigator.

Referring to FIGS. 4 aand 5 of the accompanying drawings, the handle 16 of the oral irrigator includes an elongated body member 41 having a bore 42 terminates at the inlet end of the body 41 and receives hose or conduit 15 which extends entirely through the bore. Control valve 19, described in greater detail with respect to FIGS. 6 and 7, is rotatable to controllably crimp hose 15 within bore 42.

A collar 43 is secured to the outlet end of body 41. Collar 43 is an elongated hollow member having an interior annular shoulder adapted to abut the end of the body member. The body 41 and collar 43 are secured to one another by suitable adhesive or the like. A hose-to-stem adapter 44 fits in and is secured to the interior of collar 43. One end of adapter 44 is in the form of a barbed fitting 45 which extends into bore 42 to engage the end of hose 15. The other end of adapter 44 serves as a receptacle which receives stem 17 in a snap-fit engagement. a liquid flow path exists from hose 15 through adapter 44 to stem 17, the flow in said path being controllable by control valve 19. Hose 15, in turn, includes a longitudinal bore which delivers the liquid to spray head 18.

A hole 40 is defined through one side of body member 41 and communicates with bore 42. Control valve 19 extends into hole 40 where it engages and controllably crimps hose 15 in a manner best illustrated in FIGS. 6 and 7 to which reference is now made. Control valve 19 includes a knob 51 residing outside body member 41 and an operative section extending into body member 41 and across bore 42. The operative section of the control valve includes a first cylindrical section 52 adjacent knob 51 and having a diameter substantially equal to that of hole 40 in which cylindrical section 52 resides. An intermediate section 53 of substantially narrower diameter than section 52 extends longitudinally from section 52 but longitudinally off-center relative to the longitudinal axis of section 52. Another cylindrical section 54 of the same general diameter as section 52 extends longitudinally from section 53, and a stub section 55, disposed coaxially with sections 52 and 54, extends from section 54. Hole 40 in the handle body includes an annular shoulder adapted to abut section 54 of the valve so that stub 55 is journaled in a reduced diameter portion of the hole.

Hose 15 extends through valve 19 between sections 52 and 54. The diameter of valve section 53 is such that hose 15 may extend thereby in bore 42 without being crimped, as illustrated in FIG. 6. However, if the valve is rotated 180°, the eccentric or off-axis nature of section 53 permits it to crimp and entirely block liquid flow through the hose. Intermediate positions (between 0° and 180°) of the valve provide partial crimping of the hose so that liquid flow can be controlled over a continuous range.

It is noted that valve 19 is actually held in place by its engagement of hose 15. During assembly, valve 19 is inserted into hole 40 and hose 15 is then snaked through bore 42 with valve 19 in its open position.

Referring specifically to FIGS. 8, 9 and 10, the rigid plastic oral irrigator stem 17 terminates in a sweep head 18. The sweep head includes a main body portion 81, including a downwardly projecting annular sleeve adapted to receive and be bonded or otherwise secured to the end of stem 17. The upper surface 80 of body 81 has a fluidic oscillator element defined therein as best illustrated in FIG. 10. A flat cover 82 is bonded to surface 80 to seal the fluidic oscillator channels defined in that surface. A lid member 83 fits over and is bonded to cover 82 and extends down along the sides of body member 81 to which it is also bonded.

The fluidic oscillator comprises a plurality of flow passages and fluid interaction areas in the form of channels defined in surface 80 of body member 81. The oscillator is preferably the same oscillator which is the subject of U.S. patent application Ser. No. 510,722, filed on concurrent date herewith by Ronald Stouffer and Harry Bray, and entitled "Improvements in Controlled Fluid Dispersal Techniques". Although described hereinbelow to some extent, the oscillator and its operation are more fully described in the aforementioned patent application which is incorporated herein by reference.

The fluidic oscillator includes a power nozzle 90 adapted to receive pressurized liquid from the bore in stem 17 through a suitably provided passage 84 defined through body member 81. Power nozzle 90 issues a power stream of the pressurized liquid into the upstream end of an interaction region 91. The interaction region is open at its upstream end to receive the power stream and has an open throat 92 at its downstream end through which the power stream egresses. Throat 92 is axially aligned with power nozzle 90. The sides of interaction region 91 are bounded by left sidewall 93 and right sidewall 94. These sidewalls first diverge from power nozzle 90 in a downstream direction and then converge toward throat 92.

An outlet region 95 is located downstream of throat 92 and is bounded by left and right outlet walls 96 and 97, respectively. These outlet walls diverge in a downstream direction from throat 92 over the entire length of the outlet region. A left control passage 98 is defined between an opening 99 in left outlet wall 96 and a left control port 101 defined through left sidewall 93 at the upstream end of interaction region 91. Similarly, a right control passage 102 is defined between an opening 103 in right outlet wall 97 and a right control port 104 defined through the right sidewall 94 at the upstream end of the interaction region. The sections of outlet walls 96, 97 which are downstream of openings 99 and 103 diverge at a somewhat smaller angle than the outlet wall sections upstream of these openings. The reason for this is described subsequently.

The oscillator is symmetrical about an imaginary longitudinal axis extending through the centers of power nozzle 90 and throat 92. In other words, sidewalls 93 and 94 are mirror images of one another, as are control passages 102, 98 and outlet walls 96 and 97.

The throat 92 is preferably just slight wider than the width of the power nozzle 90 at its narrowest point. The width of the control passages 98 and 102 is smaller than that of nozzle 90 and preferably on the order of one half the power nozzle width. The distance between the power nozzle 90 and throat 92 is short compared to conventional oscillators. If the width of power nozzle 90 at its narrowest point is W, if the width of throat 92 at its narrowest point is T, if the distance between the narrowest points of nozzle 90 and throat T is D, and if the width of the control passage is X, then the following relationships are suitable, although not exclusive, for an operable oscillator:

$$T = 1.1W \text{ to } 1.5W$$

D = 5W to 8W
X ≤ 0.75W

In an actual embodiment which was tested and operated satisfactorily, W = 1.1 mm, T = 1.35 mm, D = 7.3 mm, X = 0.65 mm, and the depth of all channels in surface 80 was 0.5 mm. It is understood for the foregoing dimensions that the channel depth is assumed to be constant throughout the entire oscillator; however, channel depth may vary throughout the oscillator and the widths can be changed accordingly to provide equivalent cross-sectional areas.

The operation of the fluidic oscillator is such that the power jet alternately flows along left sidewall 93 and right sidewall 94, much the same as in many conventional prior art fluidic oscillators. However, there are significant distinctive operating features of this oscillator. Specifically, because of the relatively narrow throat 92, the oscillating power jet acts to seal the interaction region 91 off from static pressure conditions in the outlet region 92. In addition, the relatively short interaction region 91 and the relatively narrow control passages 98 and 102 combine with the sealing effect to produce a static pressure at the upstream end of the interaction region which is positive relative to the static pressure in outlet region 92. As a consequence of this pressure difference, water tends to flow through control passages 98 and 102 in a direction from the interaction region 91 toward outlet region 95. In fact, control passages 98 and 102 remain filled with water during the entire operation of the oscillator. More particularly, if it is initially assumed that the power jet is flowing along left sidewall 93, the jet is directed generally toward the right outlet wall 97 as it exits from throat 92. The power jet acts to entrain water from control passage 102 as the jet passes opening 103, and the relatively positive static pressure in the region of control port 104 continues to supply water to passage 102 for such entrainment. This relatively positive static pressure is also present at control port 101; however, since the power stream does not entrain liquid from passage 98 at this time, a convex meniscus of liquid tends to bulge outwardly from opening 99, the passage 98 remaining filled with liquid. Due to the entrainment of liquid by the power stream at opening 103 and the absence of such entrainment at opening 99, a differential pressure is created across the power jet at control ports 101 and 104 in a sense to deflect the jet to flow along right sidewall 94. A similar operation ensues with the power jet now entraining liquid from control passage 98 and a liquid meniscus developing at outlet opening 103 of liquid-filled passage 102. The differential pressure between the control ports 101 and 104 reverses and oscillation of the power stream ensues.

An interesting phenomenon of the oscillator relates to the action of the meniscus on the power jet as it sweeps across the outlet region. Specifically, as the sweeping jet approaches the meniscus, the latter tends to break up and the liquid therefrom merges with the jet. The flow from the control passage which thus merges with the power jet prevents the jet from impingeing against the outlet wall. As a consequence, there is no shearing of the jet by the outlet wall with the result that droplets from the sweeping jet remain relatively large as compared to the finely particulated droplets produced by shearing effects.

The fact that neither liquid nor air flows into the interaction region via control passages 98 and 102 is particularly advantageous for an oral irrigator. This characteristic prevents ingestion of food particles from the user's mouth into the oscillator, which particles might tend to clog the oscillator and impair its operation.

It has been observed that the meniscus tends to become concave at outlet openings 99, 103 if the dynamic pressure of the power jet is increased beyond some pressure level. This does not affect the operation as described, however, since the liquid in the control passage still flows out to merge with the power jet in the outlet region when the jet flows past the corresponding outlet opening 99, 103.

The sweeping jet is issued from outlet region 95 into the oral cavity of the user. There is no restrictive passageway or any other element downstream of the oscillator which can introduce pressure drops in the jet. The issued jet has been found to break up into droplets of uniform size, which droplets are distributed in a uniform pattern. The uniform droplet size assures that each droplet produces a similar depression and effect as it impacts upon the user's gums; that is, successive droplets create identical effects on adjacent gum portions. The uniform pattern assures that the droplets are equally distributed along the impact path of the sweeping jet so that some locations in the swept path are not impacted to a greater or lesser degree than other locations. The overall effect of this uniformity of droplet size and spray pattern has been found to produce a more pleasurable feeling than pulsed jets and has been shown to remove dirt particles from teeth and gums at a significantly faster rate than pulsed jets. Specifically, in tests of the two types of oral irrigators, users were asked to eat the same food before using each irrigator and continue irrigation until the mouth felt clean. Results showed that the spray jet irrigator of the present invention cleans oral cavities 30% faster than a commonly available pulsed jet irrigator.

Although uniformity of spray pattern achieves desirable effects it is not crucial for satisfactory oral irrigator operation. Consequently, the oscillator may be operated in other modes, wherein the spray pattern is not necessarily uniform or evenly distributed, as taught in the aforementioned U.S. patent application Ser. No. 510,722, by Stouffer and Bray.

As noted, an important feature of the oral irrigator of the present invention is the fact that sweeping of the jet is effected in the irrigator head 18 just prior to issuance of the jet from the irrigator. While the oscillator described above is particularly advantageous for reasons already mentioned, there are numerous other ways to achieve the desired sweeping action within the scope of the present invention. For example, substantially any fluidic oscillator may be so employed, as long as it is located in irrigator head 18 and its outlet is configured as a diverging outlet region rather than as plural discrete outlet passages. Examples of such oscillators are those described in U.S. Pat. No. 3,563,462 (Bauer), U.S. Pat. No. 3,432,102 (Turner et al.), U.S. Pat. No. 3,185,166 (Horton et al.), U.S. Pat. No. 3,016,066 (Warren et al.), etc. Each of these oscillators may be appropriately sized to conform to a head 18 which readily fits and can be operatively moved in a user's mouth.

In addition to fluidic oscillators, other sweeping arrangements may be employed. For example, reference is made to FIG. 11 wherein there is illustrated a portion of a rigid stem member 110 having a central fluid conducting bore 111 defined therein. The bore terminates at the outlet end of the stem where it receives a flexible tube 112. One end of the tube is bonded or otherwise secured in the bore 111; the other end of the tube is freely suspended. Water flow through the bore 111 and tube 112 causes the outlet end of the tube to react by whipping around. If this whipping motion is constrained to a single plane, the tube sweeps back and forth at a frequency determined by the water pressure.

In FIG. 12, the sweeping arrangement of FIG. 11 is illustrated as part of an oral irrigator head 120. Specifically flexible tube 121 is fixedly mounted at one end 122 where it receives water under pressure. The other end of the tube is suspended. A bottom wall 123 and top wall (not shown) constrain the tube so that it moves only in a plane parallel to these two walls. Water issued by tube 121 is in the form of a jet which respectively sweeps back and forth as the tube ships back and forth within head 120.

Still another sweep arrangement is illustrated in FIG. 13 wherein a vibrating reed type oscillator is incorporated in an oral irrigator head 130. The oscillator includes a generally heart-shaped interaction region 131 which is open at its pointed or down stream end to provide an outlet 135 for a water jet. An outlet region 136 is located downstream of outlet 135 and is bounded by diverging outlet walls 137, 138. Inlets 132, 133 for pressurized water are located in respective lobes of heart-shaped chamber 131 and are arranged to receive pressurized water from an irrigator stem (not shown) in the manner described in relation to the fluidic oscillator head of FIGS. 8–10. Interaction region 131 is formed as a channel in one plate of head 130 and is covered and sealed by another plate not shown.

A vibratable reed 134 extends longitudinally through chamber 131 and is fixed to the upstream end of the chamber. The other end of reed 134 is freely suspended and extends into outlet region 136. The width of the reed (i.e. — the dimension perpendicular to the plane of the drawing) is just slightly smaller than the depth of the channel from which the interaction region 131 is formed. The reed thus divides interaction region 131 into two sub-chambers 139, 140.

In operation, the reed 134 is alternately driven from side to side in the interaction by the alternating and oppositely phased build up and relaxation of pressure on both sides of the reed. For example, in the position of the reed shown in solid side of FIG. 13, wherein the reed is against outlet wall 138, sub-chamber 139 is sealed off from outlet 135 by the reed. Consequently the pressure builds up within sub-chamber 139. Sub-chamber 140 on the other hand has complete access to outlet 135 so that outflow from sub-chamber 140 avoids pressure build-up therein. The differential pressure between the two sub-chambers deflects the reed again. Oscillation of the reed continues in this manner.

Outflow from the interaction region is in the form of a water jet directed in accordance with the position of the reed. For example, when the reed is against outlet wall 138, outflow from sub-chamber 140 is directed by the reed and by the sub-chamber sidewall to flow along the reed. As the reed begins deflecting toward outlet wall 137, flow from sub-chamber 140 remains directed along the reed, the directivity being aided by the boundary layer attachment or Coanda effect along the reed. In addition, as the reed moves from outlet wall 138, outflow begins and gradually increases from sub-chamber 139. This outflow is also guided by the reed and by the curvature of the sidewall in sub-chamber 139. The individual jets from the two sub-chambers merge just downstream of the termination of reed 134 due to the low pressure region created at the reed tip by the aspiration action of the flowinng streams. The merging of the two streams forms a single jet which is thus swept by the reed as it oscillates back and forth. Depending upon the material and dimensions of the reed and upon the pressure of the water, high frequencies may be readily achieved.

Numerous other jet-sweeping arrangements are feasible within the scope of the present invention. The important feature is that the jet itself be swept, not the irrigator head. By sweeping the jet and not the head, higher sweep frequencies can be attained and it is the high sweep frequencies which bring about faster cleaning rates and more effective and pleasurable gum massaging than is obtained with the pulsed jet oral irrigator.

As an adjunct to the present invention it is possible to combine brushing and irrigating functions in the same device. For example, rigid bristles may be secured to the head about outlet opening 95 in the oscillator of FIG. 9. Such bristles tend to vibrate due to vibrations set up in the head by the oscillations of the jet. The bristle vibrations may be used for cleaning and massaging functions. Of course, the user of such a device may also move the head and bristles to effect tooth brushing in a conventional manner.

In summary, the swept jet oral irrigator of the present invention provides fast cleaning and pleasurable gum massaging functions. The sweeping of the jet itself permits higher pressure delivery than in irrigators which require pulsed jets to traverse long stems after the oscillating function is performed. In addition, the unit is capable of continued sweeping while submerged in water so that operation continues even if the user's mouth is closed about the head.

While we have described and illustrated one specific embodiment of our invention, it will be clear that variations of the details of construction which are specifically illustrated and described may be resorted to without departing from the true spirit and scope of the invention as defined in the appended claims.

We claim:

1. An oral irrigator comprising:
fluid conduit means adapted to receive and conduct pressurized liquid;
handle means including an internal fluid passage arranged to receive pressurized liquid from said fluid control means; and
a head member adapted to receive pressurized liquid from said fluid passage, said head member being of a size suitable for insertion into the oral cavity of a user of said oral irrigator, said head member including:
jet-defining means responsive to pressurized liquid received by said head member for defining a jet of said liquid;
cyclical sweep means for cyclically sweeping said jet over a prescribed path at a frequency in excess of two thousand cycles per minute; and
outlet means for issuing the cyclically swept jet in a sweeping pattern;
wherein said internal fluid passage in said handle means includes a bore extending through said handle means, wherein said fluid conduit means extends into said bore, and wherein said control valve includes means for selectively crimping said fluid conduit means in said bore.

2. An oral irrigator comprising:

fluid conduit means adapted to receive and conduct pressurized liquid;

handle means including an internal fluid passage arranged to receive pressurized liquid from said fluid conduit means; and a head member adapted to receive pressurized liquid from said fluid passage, said head member being of a size suitable for insertion into the oral caviity of a user of said oral irrigator, said head member including:

jet-defining means responsive to pressurized liquid received by said head member for defining a jet of said liquid;

cyclical sweep means for cyclically sweeping said jet over a prescribed path at a frequency in excess of 2000 cycles per minute; and outlet means for issuing the cyclically swept jet in a sweeping pattern;

wherein said cyclical sweep means comprises a fluidic oscillator including:

an interaction region having an upstream end, a downstream end, and left and right sidewalls which first diverge from said upstream end and then converge toward said downstream end to define an exit throat at said downstream end, the space between said sidewalls being completely open to provide a direct and unobstructed flow path between said upstream and said exit throat;

a power nozzle positioned to direct said jet into said interaction region through said upstream end;

an outlet region corresponding to said outlet means, located downstream of said exit throat and defined between left and right outlet walls which diverge from said throat; and left and right control passages extending between said outlet region and the upstream end of said interaction region, said left control passage opening into said interaction region through said left sidewall and into said outlet region through said left outlet wall, said right control passage opening into said interaction region through said right sidewall and into said outlet region through said right outlet wall.

3. The oral irrigator according to claim 2 wherein said fluidic oscillator is further characterized in that for a power nozzle width of W at its narrowest point, said throat has a width on the order of 1.1W to 1.5W, the distance between said nozzle and throat at their narrowest points is on the order of 5W to 8W, and the control passages are substantially narrower than W, whereby during normal operation of the oscillator the static pressure at the upstream end of said interaction region becomes positive relative to the static pressure at said outlet region.

4. The oral irrigator according to claim 2 wherein said fluidic oscillator is further characterized in that said exit throat is only slightly larger than said power nozzle in order that the jet exiting said interaction region may seal off said interaction region from said outlet region, wherein said interaction region is sufficiently short and the cross-section of said control passages are sufficiently small to create a positive static pressure at the upstream end of said interaction region relative to the static pressure in said outlet region whereby said control passages remain filled with said liquid and flow through control passages is in a direction toward said outlet region during operation of the oscillator.

5. The oral irrigator according to claim 2 including means for creating a positive static pressure at the upstream end of said interaction relative to the static pressure at said outlet region during operation of said irrigator during operation of the oscillator to cause liquid to flow through said control passages in a direction toward said outlet region.

6. A method of cleaning teeth and massaging gum tissue in an oral cavity using an oscillator of the type in which a liquid jet is issued into the upstream end of an interaction region having a single outlet throat and two sidewalls which diverge from said upstream and then converge toward said outlet throat, said method comprising the steps of:

delivering pressurized liquid to said upstream end of said interaction region;

repetitively sweeping said jet back and forth between said sidewalls such that said jet, while sweeping, remains integral and undivided within said interaction region, said sidewalls serving to guide said jet and to define extreme positions of the jet sweep; and issuing the swept jet through said outlet throat against surfaces to be treated in an oral cavity.

7. The method according to claim 6 wherein the sweep frequency of said jet is on the order of 20,000 cycles per minute.

8. The method according to claim 6 wherein the step of sweeping is performed by a relatively stationary member which is inserted into the user's oral cavity during the performance of said method.

9. An oral irrigator for issuing a pressurized liquid into the mouth of a user in order to massage gum tissues and dislodge food particles, said oral irrigator comprising:

a handle;

a head portion adapted to be secured to said handle and of sufficiently small size to be inserted in the mouth of the user; and means for delivering liquid under pressure to said head portion;

wherein said head portion includes:

a nozzle arranged to receive pressurized liquid delivered to said head and issue a liquid jet;

a flow chamber having a single inlet positioned to receive said liquid jet from said nozzle and having only one outlet for said jet, said outlet being substantially aligned with said nozzle to conduct flow through said chamber to externally of said head portion, said chamber having opposite sidewalls which first diverge from said nozzle and then converge toward and terminate at said outlet, the space between said sidewalls being completely open so that a direct unimpeded flow path exists between said nozzle and said outlet; and sweep-producing means powered solely by said jet for cyclically sweeping said jet between said sidewalls in said chamber and across said outlet;

whereby said jet, upon issuance from said outlet, forms a cyclically sweeping spray pattern emanating from said head portion.

10. The oral irrigator according to claim 9 wherein said sweep-producing means comprises a fluidic oscillator incorporating said flow chamber.

11. An oral irrigator for issuing a pressurized liquid into the mouth of a user in order to massage gum tissues and dislodge food particles, said oral irrigator comprising:
a handle;
a head portion adapted to be secured to said handle and of sufficiently small size to be inserted in the mouth of the user;
means for delivering liquid under pressure to said head portion;
wherein said head portion includes:
a nozzle arranged to receive pressurized liquid delivered to said head and issue a liquid jet;
a flow chamber having a single inlet positioned to receive said liquid jet and having only one outlet for said jet, said outlet being positioned to conduct flow therethrough externally of said head portion; and
sweep-producing means powered solely by said jet for cyclically sweeping said jet in said chamber and across said outlet;
whereby said jet, upon issuance from said outlet, forms a cyclically sweeping spray pattern emanating from said head portion; and
wherein said sweep-producing means is a movable member which is driven into cyclical sweeping motion by said jet and, when so sweeping, sweeps said jet in said chamber.

12. The method according to claim 6 wherein said step of repetitively sweeping is performed by a movable member in said interaction region, said method further comprising the steps of:
driving said movable member into repetitively sweeping motion with the pressurized liquid delivered to said upstream end of said interaction region; and
sweeping the jet with said movable member.

13. The method according to claim 6 wherein said oscillator is a fluidic oscillator having no moving parts.

14. An oral irrigator comprising:
fluid conduit means adapted to receive and conduct pressurized liquid;
handle means including an internal fluid passage arranged to receive pressurized liquid from said fluid conduit means; and
a head member adapted to receive pressurized liquid from said fluid passage, said head member being of a size suitable for insertion into the oral cavity of a user of said oral irrigator, said head member including:
jet-defining means responsive to pressurized liquid received by said head member for defining a jet of said liquid;
cyclical sweep means for cyclically sweeping said jet over a prescribed path at a frequency in excess of 2,000 cycles per minute, said cyclical sweep means comprising a movable member which is repetitively swept by said issued jet and which in turn sweeps the issued jet over said prescribed path; and
outlet means for issuing the cyclically swept jet in a sweeping pattern.

* * * * *